United States Patent [19]
Froman

[11] Patent Number: 5,866,354
[45] Date of Patent: Feb. 2, 1999

[54] METHOD FOR MEASURING MOBILITY OF SPERM

[75] Inventor: David Paul Froman, Corvallis, Oreg.

[73] Assignee: The State of Oregon Acting By and Through the State of Board of Higher Education on Behalf of Oregon State University, Corvallis, Oreg.

[21] Appl. No.: 766,970

[22] Filed: Dec. 16, 1996

[51] Int. Cl.$^6$ .............................. C12Q 1/02; C12Q 1/00; G01N 33/53

[52] U.S. Cl. .............................. 435/29; 435/4; 435/975; 435/806; 436/510; 424/DIG. 14; 422/50; 564/1

[58] Field of Search ................................. 435/29, 4, 975, 435/806; 424/DIG. 14; 564/1; 422/50; 436/510

[56] References Cited

U.S. PATENT DOCUMENTS

| | | | |
|---|---|---|---|
| 5,261,870 | 11/1993 | Hammerstedt et al. | 435/29 |
| 5,304,487 | 4/1994 | Wilding et al. | 435/29 |

FOREIGN PATENT DOCUMENTS

| | | |
|---|---|---|
| WO 95/29983 | 11/1995 | WIPO . |
| WO 96/13225 | 5/1996 | WIPO . |

OTHER PUBLICATIONS

Harrison and Heald.; *The Isolation of Poly–α–L–Glutamic Acid From the Oviduct of the Domestic Fowl*; Proc R. Soc. B 166:341–357 (1966) (only pp. 341 and 353 submitted). Month Not Available.

Sokoloski et al.; *Turbidimetric Analysis of Human Sperm Motility*; Fertility and Sterility 28:12;1337–1341 (1977). Month Not Available.

Bilgili and Renden; *Fluorometric Determination of Avian Sperm Viability and Concentration*; Poultry Science 63:2275–2277 (1984). Month Not Available.

Wishart and Ross; *Characterization of a Spectrophotometric Technique for the Estimation of Fowl and Turkey Sperm Motility*; Gamete Research; 11:169–178 (1985). Month Not Available.

Nycomed brochure entitled *Isolation of Mammalian Cells*; (1987). Month Not Available.

Nycodenz® brochure entitled *Accu–Specs Sheet*; Accurate Chemical & Scientific Corporation; date of publication (1987). Month Not Available.

Serafini et al.; *Enhanced Penetration of Zona–Free Hamster Ova by Sperm Prepared by Nycodenz and Percoll Gradient Centrifugation;* Fertility and Sterility 53:551–555 (1990). Month Not Available.

(List continued on next page.)

*Primary Examiner*—Louise N. Leary
*Attorney, Agent, or Firm*—Klarquist Sparkman Campbell Leigh & Whinston, LLP

[57] ABSTRACT

A method of identifying highly fecund males in which an isotonic, buffered liquid test specimen of semen is layered on top of a barrier medium that inhibits net movement (migration) of less mobile sperm into the barrier medium. Differences in mobility of populations of sperm among test subjects have been found to predict whether a male will be highly fecund or not. Sperm migration into the barrier medium is quantitated, for example by analyzing the barrier medium in a spectrophotometer or a photometer after sperm migration is allowed to occur. Alternatively, a collection member coated with a sperm binding protein may be placed below the barrier medium, and the number of sperm that bind to the collection member quantitated after incubation. The invention also includes a device for incubating the barrier medium at a physiologic temperature for a sufficient period of time to allow the highly mobile sperm to migrate into the barrier medium. A suction device is positioned to rapidly remove the test specimen and barrier medium from the collection member, to provide an accurate and reproducible end point to the assay.

31 Claims, 5 Drawing Sheets

OTHER PUBLICATIONS

Van der Zwalmen et al.; *Sperm Morphology and IVF Pregnancy Rate: Comparison Between Percoll Gradient Centrifugation and Swim–up Procedures*; Hum. Reprod. 4:581–588 (1991)—only computer abstract submitted. Month Not Available.

Lin et al.; *Recovery of Motile Sperm Using the Osmolality–Gradient Technique*; Archives of Andrology 27:177–184 (1991). Month Not Available.

Ohashi et al.; *Preparation of Oligozoospermic and/or Asthenozoospermic Semen for Intrauterine Insemination Using the SpermPrep Semen Filtration Column*; Fertility and Sterility 57: 866–870 (1992). Month Not Available.

Hammerstedt et al.; *Artificial Insemination Using Extended Liquid Semen: An Old Technology of Great Value to Modern Industry*; The Pennsylvania State University (Manuscript, publication particulars uncertain) (1992). Month Not Available.

Almagor et al.; *Simultaneous Swim–Up/Swim–Down of Sperm in Assisted Reproduction Procedures*; J. Assisted Reprod. and Genetics 10:261–265 (1993). Month Not Available.

Amann and Hammerstedt; *In Vitro Evaluation of Sperm Quality: An Opinion*; J. of Andrology 14;397–406 (1993). Month Not Available.

Froman et al.; *Desialylation of the Rooster Sperm's Glycocalyx Decreases Sperm Sequestration Following Intravaginal Insemination of the Hen*; Biology of Reproduction 50:1094–1099 (1994). Month Not Available.

Mortimer; *Sperm Recovery Techniques to Maximize Fertilizing Capacity*; Reprod. Fertil. Dev. 6:25–31 (1994). Month Not Available.

Suttiyotin and Thuaites; *Evaluation of Ram Semen Motility by a Swim–Up Technique*; J. of Reprod. and Fertility 97: 339–345 (1993). Month Not Available.

Chan et al.; *Selection of Human Spermatozoa by a Hyperosmotic Two–Layer Percoll Gradient*; Fertility and Sterility 61:1097–1102 (1994). Month Not Available.

Matsuoka, et al.; *Comparison of Sperm Preparation Methods—Wash and Concentration, Swim–up, Migration–Gravity Sedimentation, 80% Percoll and Semen Filtration Column*; J. of Reprod. Med.40:342–346 (1995). Month Not Available.

Moohan et al.; *A Simple Technique to Quantify Human Sperm–Zona Pellucida Binding Assays*; ID Hum. Reprod. 2386–2389 (1995) (only computer abstract submitted). Month Not Available.

McLean and Froman; *Identification of a Sperm Cell Attribute Responsible for Subfertility of Roosters Homozygous for the Rose Comb Allele*; Biology of Reprod.54:168–172 (1996). Month Not Available.

Froman and McLean; *Objective Measurement of Sperm Mobility Based Upon Sperm Penetration of Accudenz®*; Poultry Science 75:776–784 (1996). Month Not Available.

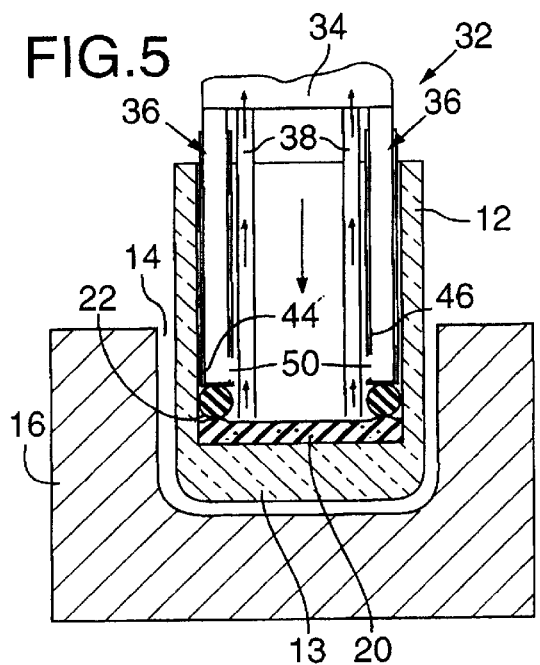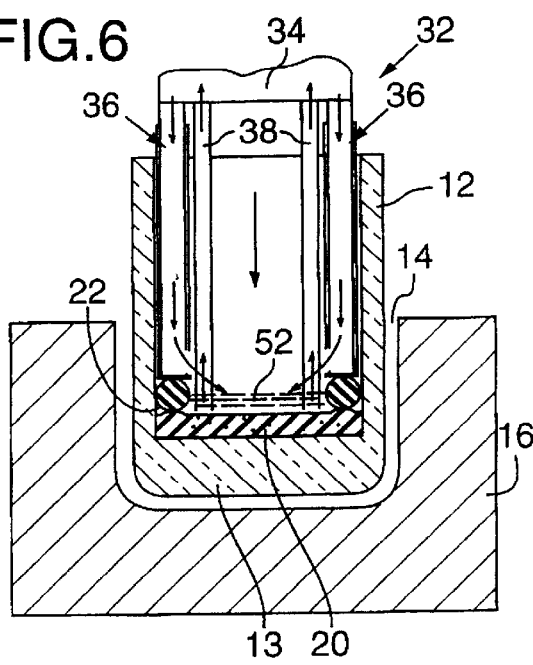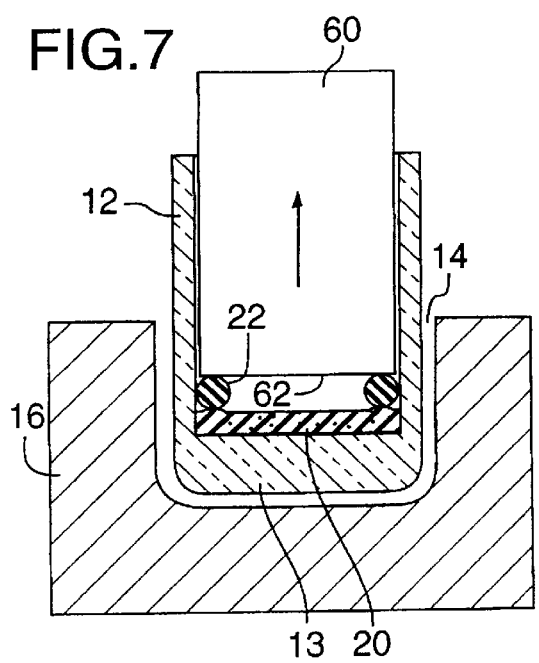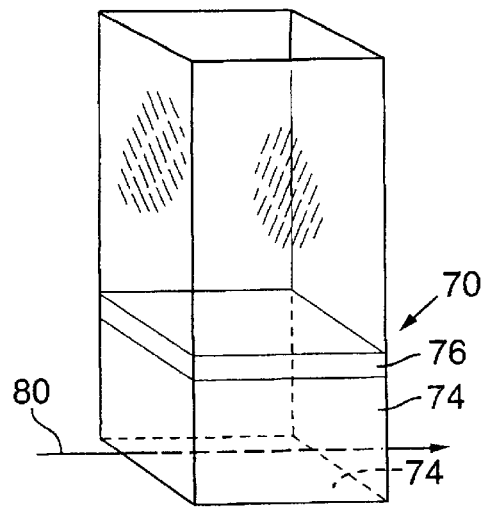

METHOD FOR MEASURING MOBILITY OF SPERM

FIELD OF THE INVENTION

This invention concerns a method of improving breeding and poultry operations by identifying highly fecund males within a population of males having previously unknown reproductive potential.

BACKGROUND OF THE INVENTION

Commercial breeding and egg-laying operations have long sought to identify highly fecund males that would be effective breeders. A "fecund" male is one capable of producing many offspring, as opposed to a "fertile" male, which is merely capable of producing offspring. The identification of highly fecund animals is very important to the profitable operation of commercial breeding businesses. High producing males, whose sperm reliably fertilizes female eggs, improve the productivity and profitability of breeding and laying operations. A variety of techniques have been used to improve male productivity, including artificial insemination and semen evaluation.

Aside from relying on historical data demonstrating fecundity of males, many techniques have been developed to attempt to predict fecundity of a male from examination of a seminal sample. Tests evaluating percentages of motile sperm, ion characteristics of sperm, or membrane integrity have been moderately useful but not reliably predictive of effectiveness as a breeder. Morphological examination and characterization of sperm has also been helpful, because morphologically normal sperm are more likely to be fertile. However tests evaluating these characteristics of sperm have been much more effective at distinguishing sub-fertile males from normal males, without identifying the relatively few males (top 30%) who will be the most effective breeders. Given the many morphologic, anatomic, and physiologic variables that are involved in fertilization, some experts in this field have declared that it does not appear possible to predict fertility of a male from a semen sample in the absence of historical breeding data.

The identification or isolation of motile sperm has been extensively studied in both human and veterinary medicine. The widespread adoption of assisted insemination, such as intrauterine insemination, gamete intrafallopian transfer (GIFT), or in vitro fertilization (IVF) for infertile human patients, has particularly stimulated the development of techniques for isolating, from an individual donor, a sub-population of sperm that has increased fertilizing capacity. One such assay involves layering a liquid medium on top of a semen sample, and allowing the sperm to swim-up into the medium. The sperm are then recovered and evaluated for concentration, motility and morphology. Almagor et al., *J. Assisted Repro. and Gen.* 10:261–265 (1993). Alternatively, sperm for in vitro fertilization can be selected by centrifuging sperm samples through gradients of Percoll solution. Chan et al., *Fertil. and Steril.* 61:1097–1102 (1994).

The quality of sperm from oligospermic and asthenospermic males has also been improved by allowing sperm in a seminal specimen to migrate through a tube that contains polysaccharide beads that develop rough surface ridges after hydration. Abnormal sperm are delayed from penetrating the column's pores by these ridges, which selectively allows motile sperm to be filtered out of the column. Ohashi et al., *Fertil. and Steril.* 57:866–870 (1992). The authors of this study reported that it was effective at slightly improving conception in infertile couples, resulting in conception in 2 out of 21 couples where the male was oligospermic.

Motile sub-populations of human sperm from an individual donor have also been isolated by suspending the sperm in a hypoosmotic medium (210 mOsm/kg) that is overlaid on an isolation medium of higher osmolality (360 mOsm/kg), that in turn overlays a recovery medium having an osmolality (290 mOsm/kg) identical to that of human uterine fluid. Motile sperm swim downward from the hypoosmotic medium toward the physiologically suitable medium (290 mOsm/kg), through interface barriers, to isolate motile sperm for IVT or GIFT. Lin et al., *Arch. Androl.* 27:177–184 (1991). This method is said to selectively isolate highly motile sperm from ejaculates, but it is not taught to be useful in the identification of highly fecund males.

The techniques described above are used to help improve fertilization capacity of an individual (usually oligospermic) male, instead of selecting breeding stock. Moreover, many of the findings from mammalian fertility research may not be applicable to avian breeding operations, such as poultry farms, because of substantial differences between mammalian and avian anatomy and physiology. In particular, mammalian sperm requires a biochemical activation step known as "capacitation" before fertilization can occur. Hence morphologically and functionally normal appearing mammalian sperm may be incapable of fertilization because of biochemical subtleties not measured by many morphologic and functional assays.

Fertilization in poultry also differs from mammals because spermatozoal sequestration in the oviduct's sperm-storage tubules allows a hen to lay multiple fertilized eggs after a single insemination. When a hard-shelled egg is laid, the vaginal sphincter relaxes and allows the oviduct to become momentarily patent. If sperm are sequestered in the storage tubule when the oviduct opens, fertilization may occur if sperm are released concurrently with relaxation of the sphincter, and passively transported upwardly through the oviduct by muscle contraction. These differences between mammalian and avian reproduction make it difficult to extrapolate from the results of mammalian assays, and draw reliable conclusions about the use of mammalian assays in avian species such as chickens and turkeys. Moreover, these tests have been designed to assess fertility and not fecundity.

A variety of methods have previously been proposed for the objective measurement of sperm motility in animals. In one such assay, sperm cells from a test specimen are allowed to "swim-up" into a clear medium from a concentrated sperm suspension at the bottom of an optical cuvette. Highly motile sperm cause a time-dependent increase in turbidity of the medium, which can be used to determine a fraction of rapidly moving sperm and an average velocity of the sperm. The changing turbidity of the medium is recorded by a spectrophotometer as an increase in absorbance. Sokoloski et al., *Fertil. and Steril.* 28:1337–1341 (1977). This reference states that no firm correlation has been established between motility and fertilizing capacity.

A swim-up technique for evaluating ram semen motility is also described in Suttiyotin and Thwaites, *J. Repro. Fertil.* 97:339–345 (1993). In this assay, ram semen is layered at the bottom of disposable cuvettes, and overlaid with a variety of clear media. Turbidity of the overlying medium is measured using a calorimeter, and the turbidity of the medium is said to correlate with motility. This reference does not disclose a use for this motility data.

PCT publication WO 95/29983 (Hammerstedt et al.) discloses a method for testing the potential fertility of spermatozoa in a sample by incubating an aliquot of the sperm sample with a binding protein extracted from native vitelline membranes removed from chicken or turkey eggs. The number of sperm that bind to the protein are then determined by examining the surface of a substrate on which the protein is coated. The PCT publication notes that there is a direct and linear correlation between sperm binding to the protein and the fertility of the spermatozoa in the sample. This assay is an in vitro test designed to simulate in vivo binding of the sperm to egg proteins, and the assay therefore provides an index of binding capacity of the sperm. This isolated measure of fertilization capacity does not alone provide a highly predictive measure of fertilization capacity of a male from which the sample is obtained.

In spite of years of research into the identification of highly fecund avian males, and the motivation of the commercial need for such identification, a reliable assay has not been found that predicts fecundity in males not having a breeding record. These failures have provoked pessimism among expert andrologists, who have predicted that such an assay will never be found for any species. Amman and Hammerstedt, J. Androl. 14:397–406 (1993).

It is therefore an object of this invention to provide a quick and reliable assay for the ready identification of highly fecund avian males who do not already have a breeding record.

Another object of the invention is to provide a device that is capable of performing such a method in an economical and efficient manner.

These and other objects of the invention will be better understood by reference to the following drawings and detailed description.

SUMMARY OF THE INVENTION

The foregoing objects are achieved by a method of identifying highly fecund males by evaluating the mobility of populations of sperm from a male having unknown fecundity. The term "mobility" refers to movement of populations of sperm from one three dimensional medium to another, as contrasted to "motility" which refers merely to a proportion of sperm that move within a field of view. Although motility is an indication of spermatozoal viability, it has been found that motility provides inadequate information about the fecundity of a male from which the semen sample is obtained. The present invention therefore instead measures migrations of populations of sperm through a three-dimensional medium, or movement of sub-population of sperm from one three-dimensional compartment into another. The inventor has found this assay to be superior for identifying highly fecund males.

In the assay of the present invention, a semen sample containing avian sperm from a male test animal is diluted in an isotonic, buffered diluent to provide a test specimen. A liquid barrier medium, adjacent the test specimen, is sufficiently wide and dense or viscous that migration of sperm from the test specimen is slowed when the sperm enters the dense medium. Highly mobile sperm have been found to migrate from the isotonic diluent into and through the dense barrier medium faster than less mobile populations of sperm from less fecund males. The dense medium is preferably maintained at an optimum physiologic temperature for mobility of the sperm. Migration of sperm into and/or through the dense medium continues for a sufficient period of time to allow the assay to distinguish sperm from highly fecund males from sperm of less fecund males. The number of sperm that migrate into the separation medium for highly fecund males will, for example, be at least one standard deviation above the mean number of sperm from males, within a base population of 100 or more males, that are less likely to be highly fecund.

In a more particular embodiment of the method, the barrier medium is a dense medium layered on the bottom of a container, and a less dense, immiscible test specimen is placed on top of the barrier medium. The test specimen medium includes semen from a male avian test subject and a diluent that is isotonic with the specimen of sperm and buffered to a physiologic pH. The test specimen and barrier medium are sufficiently immiscible to maintain their separation along the interface between them during the time period in which the assay is performed, and longer. The density of the barrier medium is sufficiently greater than a density of the test specimen to allow highly mobile sperm to migrate into the barrier medium more quickly than sperm that are not highly mobile. The barrier medium is maintained at a preselected temperature of about 40°–41° C. for a sufficient period of time to allow highly fecund males to be identified.

The method is particularly adapted for rapid identification of highly fecund males in a commercial breeding operation by automatically quantitating migration of sperm into or through the barrier medium. Automatic quantitation may be performed either by measuring increases in optical density of the barrier medium as sperm migrate into the barrier medium, or by collection of sperm on a collection member after the sperm migrate through the barrier medium. The collection member preferably includes an extract from a vitelline membrane of turkey or chicken eggs to which poultry sperm adhere. The barrier medium is preferably Accudenz [N,N'-bis(2,3-dihydroxypropyl)-5-N-2,3-dihydroxypropylacetamido)-2,4,6-triido-isophthalamide], preferably 2–10% (wt/vol) in an aqueous solution, more preferably about 4–8% (wt/vol) of Accudenz per volume of solution.

The density of the barrier medium is preferably at least 1.005, for example 1.005 to 1.075. Particularly disclosed embodiments have calculated densities of 1.04 to 1.05. The density of the test specimen medium is less than the density of the barrier medium, and is more preferably about the density of water (for example 1.000 to 1.005) or less. In disclosed embodiments there is also a difference in density of about at least 0.005 between the specimen medium and the barrier medium, more particularly a difference of about 0.005 to 0.070, and most particularly a difference of at least 0.035.

The invention also includes a device for selecting highly fecund males, in which a container is provided with a temperature regulator for maintaining the container at a preselected physiologic temperature at which sperm mobility is optimal. A volume of liquid barrier medium is provided in the container, and a volume of liquid test specimen medium is layered on top of the barrier medium in the container. An automated device then quantitates the number of sperm that migrate into or through the barrier medium, to provide an index of the fecundity of the test animal. Specifically, the quantity of sperm detected by the automated device permits identification of highly fecund males.

In some embodiments, the automated device is a spectrophotometer that measures the optical density of the barrier medium. The optical density of the separation medium will increase linearly in direct proportion to the quantity of sperm that migrate into the medium. Alternatively, the automated device is a collection member below the barrier medium to which sperm adhere after they migrate through the barrier medium. A suction device is positioned to suction the test specimen and barrier medium off of the collection member after a preselected incubation interval to quickly terminate the assay at a desired endpoint, which helps provide reliable results. The suction device also may include a flushing mechanism for washing the collection member, prior to removing the collection member from the container.

Another aspect of the invention is a test kit that includes the container, a temperature regulator for the container, and a volume of barrier medium and test specimen medium for placement in the container.

BRIEF DESCRIPTION OF THE DRAWINGS

FIG. 5 is a view of the device of FIG. 4 after telescopic shortening of guide members to allow advancement of a cannula to the bottom of the container and complete suctioning of the barrier medium and test specimen from the container.

FIG. 6 is a view of the device of FIG. 5 showing introduction of a flushing liquid from the guide member into the container.

FIG. 7 is a view of the device of FIG. 6 showing introduction of a magnetic retention ring remover into the container.

FIG. 8 is an enlarged view of another embodiment of the invention in which the media are layered in a disposable cuvette.

DETAILED DESCRIPTION OF PREFERRED EMBODIMENTS

Figure 1:
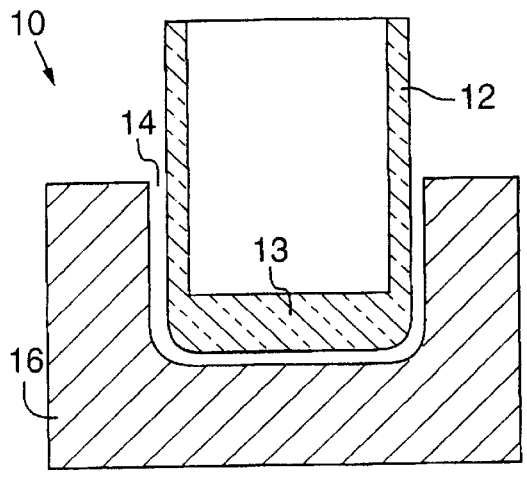
FIG. 1 is an enlarged schematic cross-sectional view of a device in accordance with the present invention for identifying highly fecund avian males.
Figure 2:
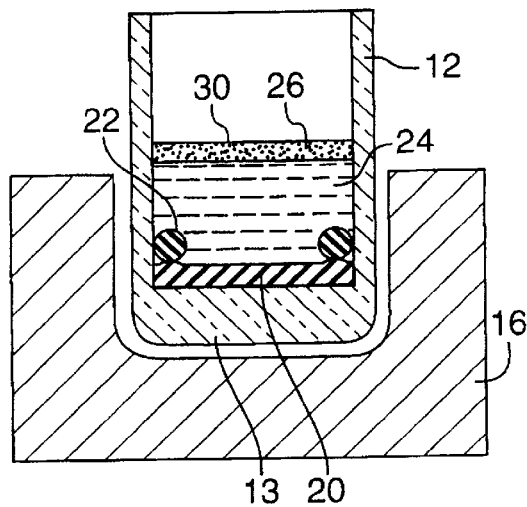
FIG. 2 is a view of the device of FIG. 1 after introducing the collection member, barrier medium and test specimen into the container.

The present invention is a method and device for identifying highly fecund avian males, such as chickens or turkeys, in a breeding operation. The assay of this invention measures the mobility of a population of poultry sperm, instead of relying on an analysis of motility of individual sperm as an indication of the fecundity of a male. The term "motility" refers to a proportion of cells that move within or within a field of view (such as a microscopic field of view). Motility is usually expressed as a percentage of the cells that are moving in the field of view.

Computer assisted sperm motion analysis can provide a rapid and precise estimate of the percentage of motile cells as well as estimates of specific averaged cellular behaviors, such as beat cross frequency (BCF; measured in Hz), velocity curvilinear (VCL; measured in micrometers per minute), velocity average path (VAP), and velocity straight line (VSL; measured in micrometers per minute). Even with such sophisticated computer assisted analysis, motility measurements have proven to be an inadequate tool to select highly fecund avian males.

The present invention has overcome the inadequate predictive power of motility measurements by measuring the mobility of populations of sperm. Mobility measurements have been found to provide superior information about the fertilizing capacity of populations of sperm, instead of focusing on the average movement characteristics of individual sperm that are measured by motility data. The term "mobility" refers to measurements of migration of sperm from a first volumetric medium to a barrier medium, for example from a first liquid layer into a second liquid layer of greater density and/or viscosity than the first liquid layer. The second liquid layer provides a physicochemical barrier to sperm migration that allows only more highly mobile sperm to move into or through the second layer.

Measurements of mobility may be qualitative or quantitative. Qualitative measurements would include visual examination of turbidity of a medium into which the sperm migrate. Quantitative measurements include photometric measurements of changes in optical density of the barrier medium, or direct measurements of absolute numbers of spermatozoal DNA adherent to a substrate adjacent the barrier medium. The number of sperm that migrate into or through the barrier medium is then used as an index of the mobility of the population of sperm from the test subject. Changes in turbidity or number of sperm adherent to a substrate are then used as an index of mobility of the test sample. In particular, test subjects having highly mobile sperm have been reliably found to be highly fecund. A highly fecund male is a test subject having a high fertility rate, as measured by the percentage of fertilized eggs produced by females of the same species inseminated with semen from the test subject. Fecundity in male poultry can also be measured by the number of fertilized eggs laid by a hen inseminated with sperm from a rooster.

Barrier media of different densities and viscosities may be used with this invention. A preferred barrier medium is a 2–10% wt/vol solution of Accudenz (a trademark for a product containing at least 98% N,N'-bis(2,3-dihydroxypropyl)-5-N-2,3-dihydroxypropylacetamido)-2,4,6-triiodo-isophthalamide available from Accurate Chemical & Scientific Corporation of Westbury, N.Y. 11590). Solutions of Accudenz in accordance with the present invention have a density of about 1.005 to 1.075. The density of the 6% (wt/vol) solution is about 1.045. It is preferably layered in a volume of 1.5 to 3.0 ml in a glass tube or cuvette, for example a cuvette having a cross-sectional area of 1 square centimeter.

A test specimen of semen containing sperm from an avian test subject is diluted in an isotonic, buffered liquid diluent. An isotonic solution is one having an osmolality of 290–325 mmol/kg of solution. The diluent is buffered to a physiologic pH of about 7.3–7.4 at which spermatozoal activity is optimal. Examples of suitable buffers include 50 mM N-tris-[hydroxymethyl]-methyl-2-amino-ethanesulfonic acid (TES), for example TES buffered saline containing 25 mM glucose and 4 mM CaCl2. The CaCl2 provides a source of calcium that optimizes sperm mobility, and the glucose provides nutrition, although they are not essential to the assay.

The test specimen contains semen that is diluted to a sperm concentration of about $1 \times 10^8$ to $10 \times 10^8$, preferably about $5 \times 10^8$. Sperm concentration of the test specimen or of the barrier medium can be determined by any method, for example comparing turbidity of diluted samples to reference optical density curves. Concentrations of live sperm also may be determined by fluorometric techniques in which the sperm containing sample is stained with ethidium bromide (EtBr), which binds double stranded, undenatured nucleic acids and induces an intense fluorescence proportional to the concentration of the stained nucleic acids. Movement of EtBr into live spermatozoa is restricted by intact cell membranes, hence live sperm are not stained and do not fluoresce. After measuring initial fluorescence, remaining cells are made permeable to EtBr by addition of 25 microliters of digitonin, which give a second fluorescence peak. Total viable sperm concentration of the sample can be estimated from a standard curve relating fluorescence units to actual sperm number, as in Bilgili and Renden, *Poul. Sci.* 63:2275–2277 (1984).

In a disclosed embodiment, in which the media are layered on top of one another in a container, the height of the barrier layer is preferably at least 3–30 mm, for example 15 mm. The volume of the barrier layer is, for example, about 1.5 ml, while the volume of the test specimen is, for example, about 0.15 ml (150 microliters). Hence the ratio of volumes of the barrier medium to the test medium is 10:1 in this disclosed embodiment. Ratios of the volumes of the two layers may vary, however, for example from 5:1 to 20:1.

The assay may be varied in numerous respects while still retaining the disclosed advantages. The density, viscosity or depth of the media may be changed, as can the concentration or number of sperm in the test sample. Although such variables will alter the time period over which the assay must be performed, the following examples provide instruction in determining this time period for any combination of such variables. The following examples also provide a scheme for identifying highly fecund avian males using this assay.

EXAMPLE 1

An automated device 10 for performing avian sperm mobility assays is shown in FIGS. 1–7. Device 10 includes a container 12 (such as a 5 ml tube) having a bottom 13 that fits within a receptacle 14 of a base 16. The base 16 may include numerous identical receptacles, although for clarity only one such receptacle is shown in the drawing. Base 16 includes a heating element that heats container 12 and its contents to a constant 40°–41° C. The constant temperature may be, for example, body temperature of the avian test subject.

To perform the assay, a collection member 20 is placed against bottom 13 of container 12, and member 20 is retained against the bottom of the tube by an O-ring 22 that extends peripherally around the inner face of bottom 13. The collection member is preferably a substrate such as a plastic, membranous, or fibrous disk that is coated with or impregnated with a protein extracted from native vitelline membranes removed from chicken or turkey eggs, as described in published patent specification WO 95/29983 which is incorporated herein by reference. More information about the extraction of this protein is provided in Example 2. The collection member 20 could also be coated with polylysine (e.g. poly-L-lysine) or polyglutamic acids to bind the spermatozoa. See Harrison and Heald, *Proc. R. Soc. B*166; 341–357 (1966) which discloses isolation of polyalphaglutamic acid, and is incorporated by reference. These polycationic materials will bind sperm.

Once the collection member 20 is secured in place under O-ring 22, barrier medium 24 (such as a 1.5–3.0 ml volume of Accudenz) is introduced into container 12, for example through a pipette or by being poured from a container. The test specimen 26 (an isotonic, buffered sperm suspension) is then similarly layered on top of barrier medium 24 at time zero.

Figure 3:
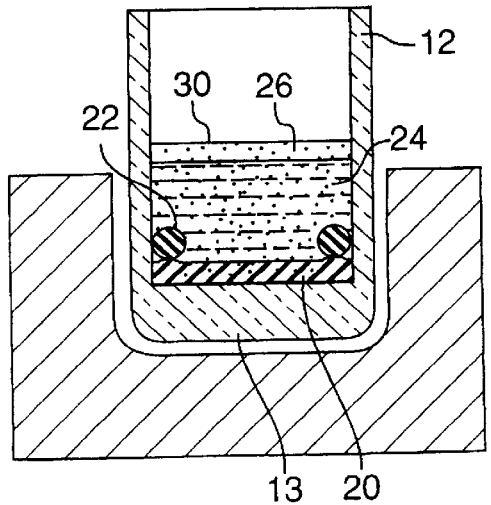
FIG. 3 is a view of the device of FIG. 2 showing migration of sperm into the barrier medium.

As shown in FIG. 3, sperm 30 migrate into barrier layer 24, and this migration increases the optical density of layer 24. Sperm that migrate into this layer also move randomly in three dimensional space, and some of these sperm adhere to collection member 20. The number of sperm that adhere to the collection member are an index of the overall mobility of the population of sperm in specimen layer 26.

The assay of the present invention typically will be performed over a period of 1 to 5 minutes, usually less than 10 minutes, during which time sperm will migrate into barrier layer 24. Accurate and reliable assay results depend on terminating the migration step promptly at a predefined point in time, for example at five minutes after introducing the test specimen medium into container 12. Termination of this step is achieved by introducing a suction device 32 into container 12, as shown in FIG. 4, to rapidly remove the media from container 12.

Suction device 32 includes a piston 34 from which depends four equally spaced, parallel, rod-shaped, telescopic guide members 36 (only two of which are shown in the drawing). The guide members are positioned to slide down along side walls of container 12 and abut against O-ring 22. Also depending from piston 34 are four equally spaced, parallel cannulas 38, one cannula 38 adjacent and parallel to each guide member 36. Each cannula 38 is connected to a vacuum source (illustrated by arrows 40 in the drawings).

Figure 4:
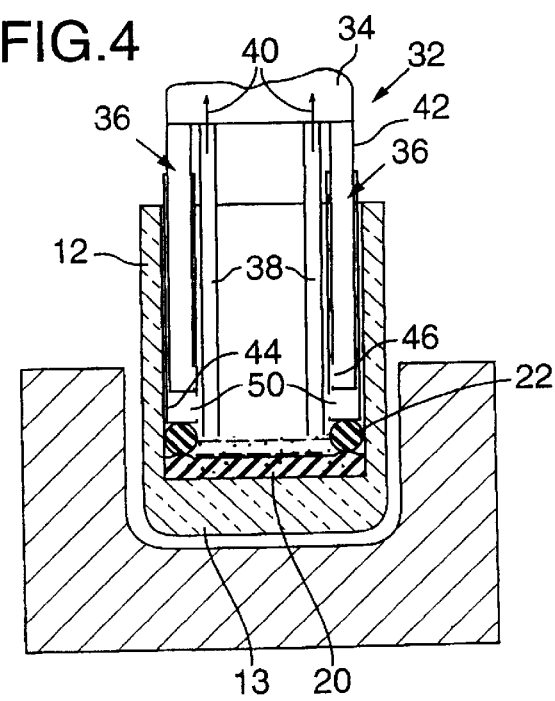
FIG. 4 is a view of the device of FIG. 3 showing introduction of the suction device into the container to remove the media.

Suction device 32 is lowered into container 12 by lowering piston 34 towards the open container, as shown in FIG. 4. Guide members 36 slide along the walls of container 12, and cannulas 38 suction the media 26, 24 out of container 12 as the suction member moves into the container. Removal of the media continues until guide members 36 abut against O-ring 22. Cannulas 38 also stop their progression with the open tip of the cannula slightly above the upper surface of collection member 20. A thin layer of media containing migrated sperm remains on the upper surface of the collection member.

Each telescopic guide member 38 includes an inner male portion 42 and an outer female portion 44. Inner portion 42 defines a peripheral vent 46 that is sealed by outer portion 44 when the guide member is in the extended position shown in FIG. 4. Outer portion 44 has a corresponding vent 50 that aligns with vent 46 when the guide member is telescoped to the position shown in FIG. 5. After the leading tips of guide members 36 abut O-ring 22, continued downward progression of piston 34 (FIG. 5) telescopes the inner portion of guide member 36 into the outer portion, to align vents 46, 50 (FIG. 6).

When vents 46, 50 align after telescopic shortening of guide members 36 as in FIG. 5, a flushing fluid (such as buffered saline or buffered water 52 in FIG. 6) is allowed to flow through the aligned vents 46, 50 on to the collection member 20 and wash any remaining media off the collection member before the collection member is removed from container 12. The flushing fluid 52 is suctioned from the container 12 through cannulas 38 after the fluid is introduced through the guide members.

After flushing is completed, suction device 32 is removed from the container by retracting piston 32. A magnet (such as piston 60 with a magnetized leading surface 62) is then introduced into the container to attract metal O-ring 22, and remove it from the container. Alternatively, the O-ring 22 may be a Teflon coated magnet, and the surface 62 of piston 60 would be a magnet of opposite polarity.

Once O-ring 22 is removed, collection member 20 may then be extracted from the bottom of container 12 and analyzed as in Example 2.

EXAMPLE 2

Collection member 20 is preferably a stiff disc-shaped plastic or other substrate that is coated with or impregnated with the protein extracted from native vitelline membranes removed from chicken or turkey eggs, as described in WO 95/29983. Alternatively, the membrane itself is layered on the substrate. The substrate is preferably made of any material, such as silicone rubber, that does not bind spermatozoa and is non-toxic to sperm.

The vitelline membrane protein extract is prepared by dissecting vitelline membranes (lamina perivitelline and lamina extravitellina) from either a group of chicken eggs or a group of turkey eggs, rinsing the membranes free of albumin and yolk, and subdividing the membranes into small particles mechanically by ultrasonic energy shearing. The resulting protein is solubilized, purified, centrifuged and concentrated to yield the protein extract in solution. The extracted protein may then be applied to the collection member 20 and allowed to dry to provide a substrate for sperm binding.

There is a correlation between sperm binding on the coated substrate, and fertilizing potential of the sperm, as described in WO 95/29983. After the assay of Example 1 is performed and collection member 20 removed from container 12, the sperm bound to the substrate are stained with 4,6-diamidino-2-phenylindole (DAP; 1 microgram/ml in PBS buffer) and examined under a fluorescent microscope. The number of sperm bound per unit area may then be counted in a magnified field, or by measuring fluorescence with a fluorometer or a plate reader. The correlation between the number of bound sperm counted and fecundity of the test subject is direct and linear.

The assay conditions described in Example 1 may be varied. For example, changes may be made in the sperm concentration, the chemical composition of the barrier layer (carboxymethyl cellulose (CMC) or bovine serum albumin (BAS) instead of Accudenz), barrier layer density, viscosity or volume, species of the test subject, period of migration (from time zero to removal and flushing of media), differences in concentration of binding protein, volume of test specimen medium, presence or absence of mobility agonists or nutrients, or other assay conditions. Given a constant set of conditions, highly fecund males may be selected by comparing the mobility of sperm from a population of male birds (e.g. 100 birds) and selecting as breeders the birds whose measured sperm mobility indicates a fecundity in a preselected range (e.g. the top 30%), as measured by relative number of sperm adherent to the collection member. That is, in a group of 100 birds, the collection members having the 30 highest rankings of numbers of adherent sperm will be considered the most fecund birds.

Depending on the degree of fecundity desired, the top 10–50% (e.g. top 20%) of birds may be selected by varying the relative number of sperm needed to satisfy the definition of "highly fecund" being used. Once a minimum number of adherent sperm is established to qualify a subject as highly fecund, then that number can be used to qualify subsequent test specimens as highly fecund, as long as assay conditions are maintained the same.

EXAMPLE 3

Another device for performing the assay of the present invention is shown in FIG. 8, wherein the container is a standard cuvette 70 made of polystyrene or other inert material. Dimensions of the disclosed cuvettes are a square cross-sectional area of 10 mm×10 mm, and a height of 45 mm, although containers of other size may be used. A collection member is not placed on the bottom surface 72 of the cuvette as in Example 1. Instead, the barrier medium (e.g. 1.5 ml 6% Accudenz or CMC) is poured into the cuvette to form the barrier layer 74 on surface 72. The isotonic buffered test specimen is then poured (e.g. in an amount of 150 microliters) on the layer 74 to form test specimen layer 76. The temperature of the cuvette is controlled (e.g. to 40–41 degrees C.) by placing the cuvette in a water bath having a regulated temperature.

After allowing sperm to migrate from layer 76 to layer 74 for a preselected period of time (e.g. 5 minutes), at the selected temperature, the cuvette is placed on a photometer or spectrophotometer and allowed to stabilize for 1 minute. An optical density of the layer 74 is then determined by measuring the absorbance of a preselected area of layer 74. A light beam 80 is directed through the layer 74 below the interface of layers 74, 76. The precise path of the light beam passing through the layer 74 is not as important as consistently directing the beam along an identical path (for example at a constant depth) through layer 74. Absorbance (e.g. at 350 nm or 550 nm wavelength) is then determined and compared to the absorbance of a reference layer 74 into which sperm have not migrated. Changes in absorbance are directly linearly related to migration of sperm into layer 74, mobility of the sperm population, and fecundity of the male from which the semen sample was taken.

Figure 13:
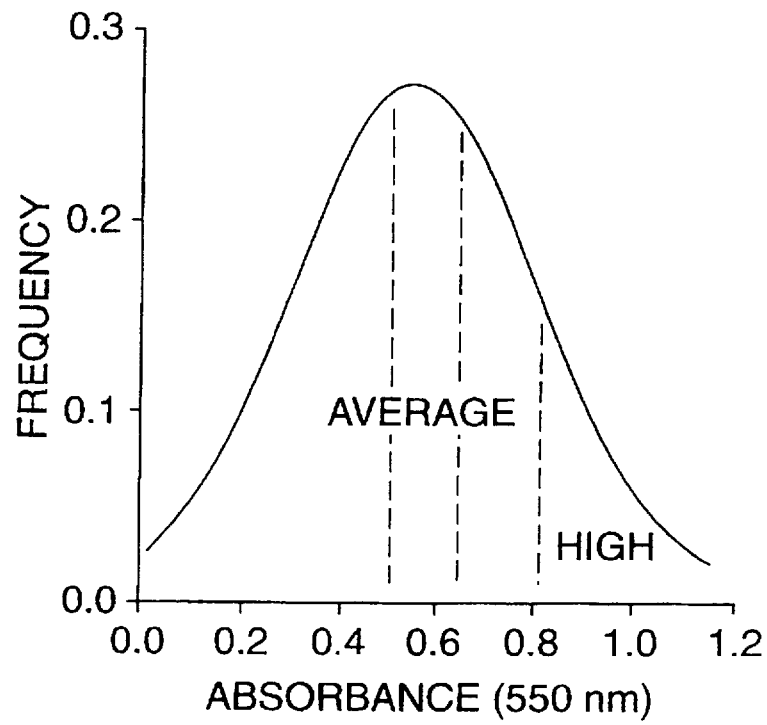
FIG. 13 is a frequency analysis graph, similar to FIG. 12, showing how the graph is used to determine absorbance values that identify highly fecund males in accordance with the conditions described in the Examples.

For any given set of assay conditions, semen samples from a group of birds (e.g. 100 roosters) can be separately assayed to produce a distribution of absorbances. Then depending on the stringency with which "highly fecund" is defined, an absorbance value is determined that establishes the desired high degree of fecundity. As shown in FIG. 13, for example, a normal distribution of frequencies of absorbances may be obtained. Then all absorbances greater than one standard deviation higher than the average absorbance of 0.6 (for example an absorbance of 0.8) would be considered the cut-off for selecting highly fecund roosters. Any specimen, assayed under the same conditions, having an absorbance equal to or greater than 0.8, would be considered to be from a highly fecund rooster.

Figure 12:
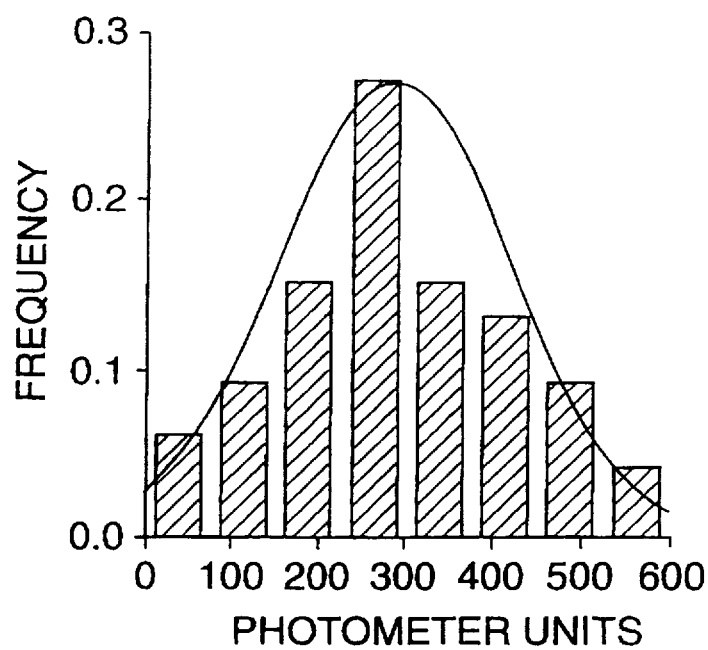
FIG. 12 is a graph of a frequency analysis of sperm mobility from 100 roosters, where photometer units indicate the extent to which sperm penetrated 6% (wt/vol) Accudenz, demonstrating a normal distribution of sperm mobilities in 100 roosters.

Instead of measuring absorbance, photometer units may instead be obtained from a photometer and used to graph a normal distribution of frequencies of that value, as shown in FIG. 12. Examination of this graph shows that choosing a photometer unit value of at least 400 would be likely to select about the top 20% of fecund males, when assays are performed with a different set of roosters under the same assay conditions. It is also helpful to repeatedly test semen samples (for example 2–4 samples from each test subject) to arrive at a mean result that even more accurately identifies highly fecund males.

EXAMPLE 4

This example establishes an intra-assay coefficient of variation, and demonstrates that sperm rendered immotile by heating do not migrate into the barrier medium. It also establishes an optimum time period for the assay to be run under the assay conditions described in this example.

Four solutions were prepared for the sperm penetration assay. First, a 30% (wt/vol) stock solution of Accudenz® was prepared with 3 mM KCl containing 5 mM N-tris-[hydroxymethyl]methyl-2-amino-ethanesulfonic acid (TES), pH 7.4, as the solvent. Another TES-based buffer, henceforth designated as motility buffer, contained 111 mM NaCl, 25 mM glucose, and 4 mM $CaCl_2$ in 50 mM TES, pH 7.4. The osmolality of the motility buffer was 320 mM/kg. A portion of the motility buffer was diluted to 290 mM/kg with deionized water. Then a 6% (wt/vol) Accudenz® solution was prepared by diluting the stock solution with diluted motility buffer. The pH and osmolality of the 6% (wt/vol) Accudenz® solution were 7.35 pH units and 323 mmol/kg, respectively.

A 1.5 ml volume of the 6% Accudenz® solution was pipetted into each of three polystyrene cuvettes 70 held within a 41° C. water bath. After the Accudenz® solution had reached thermal equilibrium, semen was procured from each of 10 New Hampshire roosters. Ejaculates were pooled and the semen thoroughly mixed. Sperm concentration was determined fluorometrically according to Bilgili and Renden, Poultry Science 63:2275–2277 (1984). Semen was diluted with motility buffer to a concentration of $5 \times 10^8$ sperm per milliliter. At 3-min intervals, a 150-$\mu$L volume of sperm suspension was overlaid on Accudenz® in a cuvette. Each cuvette was removed from the water bath after a 5 minute incubation and then placed within a spectrophotometer. Absorbance at 550 nm was recorded after a 1 minute interval by directing a light beam through the bottom centimeter of the cuvette, or more particularly through the bottom 15 mm of the cuvette. This process was repeated for sperm that had been immobilized by heating at 56° C. for 10 min. The intra-assay coefficient of variation (CV) was calculated for mobile sperm by dividing the observed standard deviation by mean absorbance and then multiplying the proportion by 100.

This procedure was replicated, but with the following modification. The bottom of each of three polystyrene cuvettes was perforated with a red-hot stainless steel probe. A 7 mm length of polyethylene capillary tubing (1.9 mm outer diameter) was attached to the cuvette with Silastic® Medical Adhesive (Dow Corning Corporation, Medical Products Division, Midland, Mich. 48640) so that the upper end of the tubing protruded 1 mm above the plane of the bottom of the cuvette. The adhesive was allowed to cure overnight. Prior to loading each cuvette with 6% Accudenz® as above, the lower end of each capillary tube was sealed with a stainless steel sealing plug. Thereafter, cuvettes were placed in a 41° C. water bath.

EXAMPLE 5

Semen was collected and manipulated as already described in Example 4. A 100-$\mu$L volume of sperm suspension was overlaid on the 1.5 ml volume of Accudenz® in a cuvette, establishing a volume ratio between the sperm suspension and Accudenz of about 1:15, with the ratio of the depths of the two layers also being about 1:15. After incubating for 10 min at 41° C., each cuvette was removed from the water bath, the stainless steel plug removed, and the Accudenz® layer collected into a 1.5 ml microcentrifuge tube. Sperm were concentrated by centrifugation at 15,600×g for 1 minute. Each supernatant was removed with a Pasteur pipet, a 40-$\mu$L volume of motility buffer was added to the microcentrifuge tube, the pelleted cells were resuspended, and the final volume of sperm suspension recorded. Likewise, residual sperm suspensions were recovered from cuvettes, volumes recorded, and sperm concentrations measured. Sperm recovered from the Accudenz® layer were expressed as a percentage of the total sperm recovered from each cuvette. A mean percentage was calculated and the intra-assay CV calculated as above.

Figure 9:
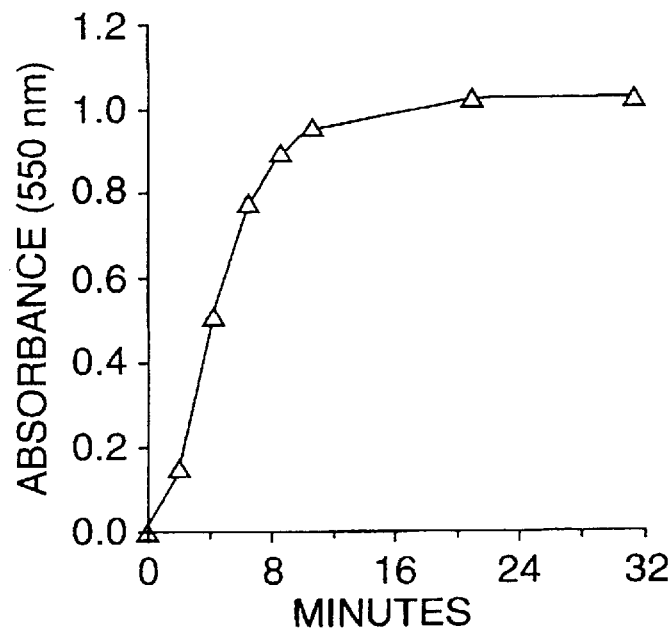
FIG. 9 is a graph demonstrating change in optical density of the barrier medium (as measured by absorbance at 550 nm in a spectrophotometer) over time after overlaying a chicken sperm suspension on the barrier medium and performing measurements at 2, 4, 6, 8, 10, 20 and 30 minutes incubation at 41° C.

Sperm rendered immotile by heating to 56° C. did not penetrate the Accudenz® layer. In contrast, motile sperm entered the Accudenz® layer rapidly and, as a consequence, absorbance increased as a function of time. A representative plot of absorbance versus time is shown in FIG. 9. Time zero denotes the time at which the 150 $\mu$L volume of sperm suspension, containing $5 \times 10^8$ rooster sperm per milliliter, was overlaid upon the 1.5 ml volume of Accudenz® prewarmed to 41° C. in a polystyrene cuvette and the initial reading made. The cuvette was returned to the water bath between measurements. Subsequent measurements were made after 2, 4, 6, 8, 10, 20, and 30 minute incubations at 41° C. When this procedure was repeated with sperm immobilized by preheating to 56° C., the absorbance remained at zero over the time course shown.

In this Example, the rate of sperm penetration was most rapid during the initial 5 minutes of incubation, as illustrated in FIG. 9. Under the conditions described in this Example, the mean absorbance, standard deviation, and coefficient of variation (n=3) were 0.9385, 0.0244, and 2.6%, respectively. When the repeatability of the assay was estimated in terms of the percentage of sperm recovered from the Accudenz® layer after 10 minutes of incubation at 41° C., the mean recovery and CV were 82% and 6.2%, respectively.

EXAMPLE 6

Example 5 established changes in optical density of the barrier medium (as a function of time) using changes in absorbance at 550 nm. This Example now shows a similar pattern of changes in optical density as measured by photometer units.

Repeated sperm mobility measurements were made on individually caged males as follows. Manual ejaculation of 48-wk-old New Hampshire roosters (n=36) was performed every-other-day. Roosters were ejaculated randomly on each of 3 consecutive semen collection days. Immediately after ejaculation, sperm concentration of each ejaculate was determined, each ejaculate diluted to $5 \times 10^8$ sperm per milliliter with prewarmed motility buffer, a 300-$\mu$L volume of the sperm suspension overlaid upon 3 ml of prewarmed 6% (wt/vol) Accudenz® held in a polystyrene cuvette, the cuvette incubated for 5 min at 41° C., the cuvette placed within a photometer (Model 534A Densimeter, Animal Reproduction Systems, Chino, Calif. 91710). Photometric data were analyzed by two-way ANOVA (Sokal and Rohlf, Biometry. W. H. Freeman and Co., San Francisco, Calif., pages 299–342, 1969).

Measurement for each ejaculate of sperm penetration into Accudenz® with a photometer (FIG. 10) produced a pattern comparable to that obtained with a spectrophotometer. Time zero in FIG. 10 denotes the time at which a 300-$\mu$L volume of a sperm suspension, containing $5\times10^8$ rooster sperm per milliliter, was overlaid upon the 3 ml volume of Accudenz® and the initial reading made. Subsequent measurements were made after 5, 10, 20, 30, and 40 minutes incubation at 41° C. These time course studies identified the pattern of migration into the medium, and therefore the optimal incubation time for taking a single reading per test subject.

When sperm mobility was tested repeatedly for each of 36 New Hampshire roosters, the effect of time was found to be an insignificant variable. However, a difference ($P\leq0.001$) in sperm mobility was found among roosters. The ANOVA is summarized in Table 1. When males were ranked by mean scores, the maximal sperm mobility score was five times greater than the minimal score.

TABLE 1

Summary of two-way ANOVA following repeated measurements of rooster sperm mobility[1]

| Source of variation | Degrees of freedom | Sum of squares | Mean square | F-value |
|---|---|---|---|---|
| Day | 2 | 8,002 | 4,001 | 1.0959 |
| Rooster | 35 | 507,096 | 14,488 | 3.9682*** |

[1]Each of 36 New Hampshire roosters was ejaculated on an every-other-day basis. Three consecutive measurements were made per rooster.
***$P \leq 0.001$.

Figure 10:
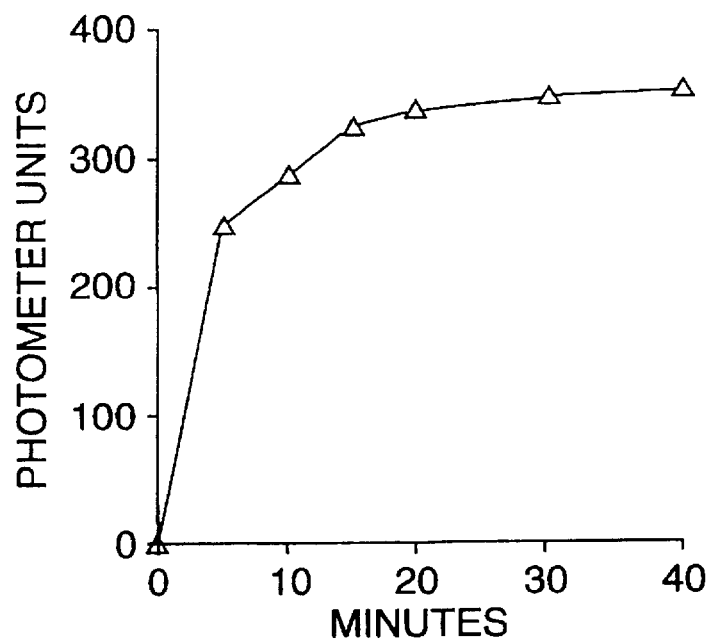
FIG. 10 is a graph similar to FIG. 9, but showing change in photometer units when the optical density of the barrier medium was measured in a photometer at 5, 10, 20, 30 and 40 minutes incubation at 41° C.

These experiments were performed with a portable photometer rather than a spectrophotometer. The photometer was suitable for use within the building in which roosters were housed, and therefore permitted an assessment of sperm mobility immediately after ejaculation. As shown in FIGS. 9 and 10, patterns of sperm penetration were comparable between instruments. Volumes of Accudenz® and sperm suspension differed between instruments due to different locations of the light beam relative to cuvette height.

Volumes used for photometry were determined empirically to simulate the pattern of sperm penetration observed with the spectrophotometer. As evidenced by ranked mobility scores and ANOVA (Table 1), appreciable differences in sperm mobility were observed among males. The rate at which sperm penetrated Accudenz® served as a basis for making distinctions among normal, fertile males, and selecting highly fecund males.

The studies in this Example could also have been performed using a photometer, such as a Turner Model 340 photometer and semi-micro cuvettes, with 600 microliters of 6% (wt/vol) Accudenz and 60 microliters of a sperm suspension containing $5\times10^8$ sperm/ml.

EXAMPLE 7

A fertility trial was performed in which 50-wk-old Single Comb White Leghorn hens (n=45 per treatment group) were inseminated with sperm obtained from the roosters categorized as having minimal, average, or maximal sperm mobility. Roosters within each category (n=3) were manually ejaculated, their semen pooled, sperm concentration measured as above, and pooled semen extended to $5\times10^8$ sperm per milliliter with motility buffer. Each hen was inseminated intra-vaginally with $5\times10^7$ sperm. Egg collection, incubation, and data analysis were performed according to Kirby and Froman, Poultry Science 69:1764–1768 (1990).

The difference in fertility between roosters categorized as having minimal or maximal sperm mobility was assumed to be 5 percentage units. The number of eggs per treatment group needed to detect this difference with 90% certainty at a significance level of $\alpha=0.05$ was calculated according to Sokal and Rohlf, Biometry. W. H. Freeman and Co., San Francisco, Calif. (1969). Thus, only roosters categorized by maximal or minimal sperm mobility were used as semen donors in this fertility trial.

Males within each category (minimal or maximal, n=3) were manually ejaculated and their semen processed as above. Prior to insemination, sperm mobility was measured as outlined in Example 6 using a 5-minute incubation interval. Then, each of approximately 130 54-wk-old Leghorn hens was inseminated intra-vaginally with $5\times10^7$ sperm from males in the minimal sperm mobility category. Thereafter, this process was repeated for males within the maximal sperm mobility category. Egg collection, incubation, and data analysis were performed as above.

Differential sperm mobility was confirmed spectrophotometrically prior to insemination. After a 5-min. incubation interval at 41° C., the absorbance of the 6% (wt/vol) Accudenz® was 0.4423 and 0.8470 for males categorized a priori as having minimal and maximal sperm mobility, respectively. A difference in fertility ($P\leq0.001$) was observed between hens inseminated with sperm from males categorized by minimal or maximal sperm mobility (Table 2). Graphical analysis of this data set (FIG. 11) revealed that the difference was attributable to lower initial fertility in the case of hens inseminated with sperm characterized by minimal mobility. Fertility of the hens was determined by the number of eggs laid by the hens following insemination.

Figure 11:
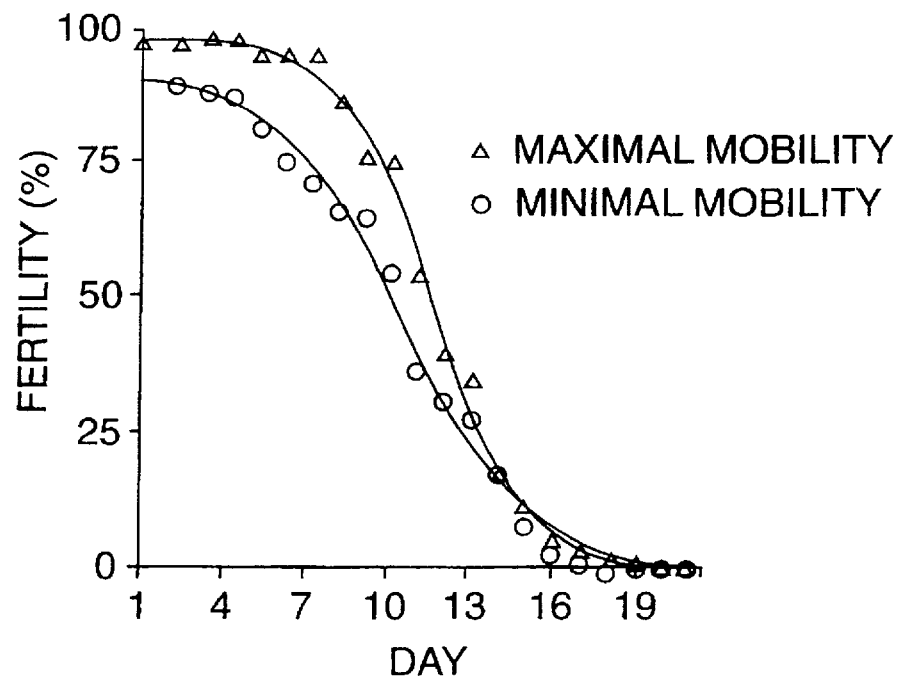
FIG. 11 is a graph of fertility versus time, demonstrating that differences in fertilizing capacity between sperm specimens of maximum mobility (triangles) and minimal mobility (circles) persist over time.

FIG. 11 shows the duration in days of fertility after a single insemination of Single Comb White Leghorn hens with sperm from New Hampshire roosters categorized as maximal ($\Delta$) or minimal ($\circ$) sperm mobility. Sperm mobility was measured by sperm penetration into 6% (wt/vol) Accudenz® solution from an overlay. Designations were based upon the ranked mean scores of 36 roosters.

When these data sets were analyzed graphically (FIG. 11), the initial level of fertility, differed by 6 percentage units, and this disparity increased over the course of a week. In fact, fertility during this interval was 894% (n=842 eggs) and 96% (n=868 eggs) for males categorized by maximal and minimal sperm mobility, respectively. Thus, although insemination doses were equivalent, the effective doses were not.

TABLE 2

Summary of fertility trial

| Roosters (n) | Sperm mobility[1] | Hens[2] | Eggs[3] | Fertility[4] (%) |
|---|---|---|---|---|
| | | ---------n--------- | | |
| 3 | Maximal | 135 | 2,590 | 52 ± 1.0[A] |
| 3 | Minimal | 129 | 2,485 | 44 ± 1.4[B] |

[A,B]in a column means values differ significantly ($P \leq 0.0001$).
[1]A priori categorization based upon sperm penetration of 6% (wt/vol) Accudenz ®. Roosters (n = 36) were ranked by mean mobility scores, and 3 representative roosters were chosen per category. Differential sperm mobility was confirmed prior to insemination. Sperm from "minimal" roosters penetrated Accudenz ® to only 51% of the extent to which sperm from "maximal" roosters did.
[2]Each hen was inseminated intravaginally with a single dose of $5 \times 10^7$ sperm.
[3]Collected over a 21-day interval.
[4]Each value is a mean ± SEM.

EXAMPLE 8

Statistical Analysis of Males Categorized by Sperm Mobility

Individually caged 25-wk-old roosters (n=100) were assigned randomly to be ejaculated on one of 3 consecutive days. Sperm mobility was measured photometrically as described above. Data were analyzed by single classification ANOVA (Sokal and Rohlf, pages 204–253) in order to determine whether observations were independent of a time effect. The Kolmogorov-Smirnov test for goodness of fit was used to determine whether observed frequencies approximated a normal distribution (Sokal and Rohlf at pages 549–620).

Males were ranked by their sperm mobility scores. Males with scores near average (n=18) were categorized as average. Males with scores greater than one standard deviation above the mean (n=17) were categorized as high sperm mobility males. Manual ejaculation of categorized roosters was initiated on an every-other-day basis. Roosters were randomized by cage number, and sperm mobility was measured photometrically on each of 3 days. Photometric data were analyzed by split-plot design ANOVA (Sokal and Rohlf at pages 343–366).

Measurements of sperm mobility from individual roosters made over a 3-day interval were independent of the day on which the measurements were made. Therefore, data were pooled and a frequency analysis performed (FIG. 12). Bars denote categories based upon the extent to which sperm penetrated 6% (wt/vol) Accudenz® as measured by a photometer. Each category represents an increment of 75 photometer units. Bars are centered upon interval midpoints. Thus, the first bar, which is centered on 37.5 photometer units, represents the frequency of observations that were $\leq$75 photometer units.

Observed frequencies approximated a normal distribution. The solid line in FIG. 12 represents the shape of the predicted distribution using 283 and 131.4 as estimates of $\mu$ and $\sigma$, respectively. When males were ranked by mobility scores, the maximum was 30.5-fold greater than the minimum. Analysis of repeated measurements from males categorized by average or high sperm mobility demonstrated highly significant differences ($P \leq 0.0001$) between categories and among males within categories (Table 3). In contrast, neither time nor a category by time interaction exerted an effect on sperm mobility.

TABLE 3

Summary of split-plot ANOVA following repeated measurements of sperm mobility from roosters categorized a priori by average or high sperm mobility[1]

| Source of variation | Degrees of freedom | Sum of squares | Mean square | F-value |
| --- | --- | --- | --- | --- |
| Category | 1 | 813,875 | 813,875 | 70.54**** |
| Males within category | 33 | 1,465,375 | 44,405 | 3.85**** |
| Time | 2 | 12,033 | 6,016 | 0.52 |
| Category by time | 2 | 28,010 | 14,005 | 1.21 |

[1]Each of 35 New Hampshire roosters was ejaculated on an every-other-day basis. Three consecutive measurements of sperm mobility were made per rooster. Roosters were categorized by average (n = 18) or high sperm mobility (n = 17) after the sperm mobility of each of 100 New Hampshire roosters had been determined by sperm penetration of 6% (wt/vol) Accudenz ®.
****P $\leq$ 0.0001.

EXAMPLE 9

Interassay Coefficient of Variation

Five representative roosters were selected from each of two sperm mobility categories as determined by the mobility assay of Example 8. Each of the five roosters was ejaculated on a weekly basis. Semen was pooled by category as roosters were ejaculated, and duplicate measurements of sperm mobility were made by spectrophotometric analysis per pool per week. A different batch of reagents was used each week. Interassay coefficients of variation (CV) were estimated from the sample means of each category.

Mean absorbance, standard deviation, and interassay CV (n=3) for roosters categorized by photometry as having average sperm mobility (see FIG. 12) were 0.5614, 0.10133, and 18.0%, respectively, when the sperm mobility of pooled semen was evaluated by spectrophotometry. Likewise, these statistics were 1.0082, 0.09256, and 9.2% for roosters categorized by high sperm mobility. Sperm from average roosters penetrated the Accudenz® layer to only 55±5.9% of the extent to which sperm from high sperm mobility roosters did.

EXAMPLE 10

The Examples set forth above show that with roosters the mobility assay of the present invention will: 1) approximate physiological conditions; 2) require simple, portable equipment; 3) be applicable to individual males; and 4) yield repeatable, biologically significant results. Furthermore, the assay can be used with sperm from other birds, such as turkey sperm, as illustrated in this Example.

Figure 14:
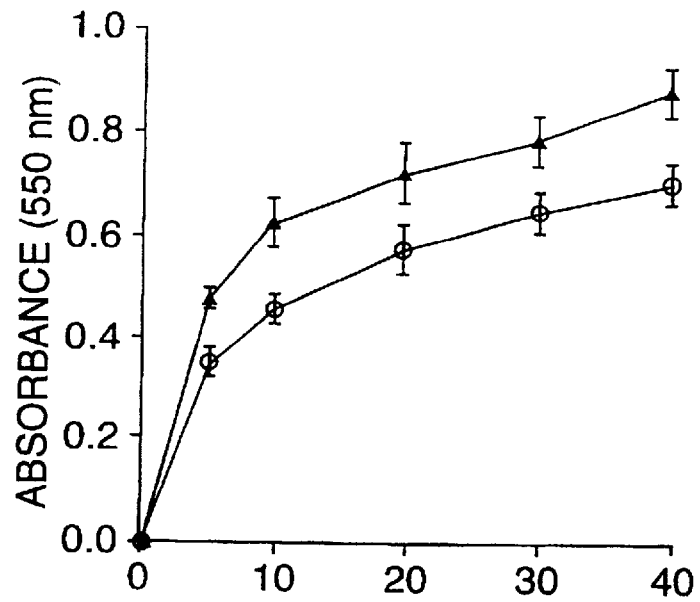
FIG. 14 is a graph of absorbance of 4% (wt/vol) Accudenz over time after overlay of pooled turkey semen on the Accudenz, showing that an exogenous motility agonist (caffeine) can increase sperm mobility.

FIG. 14 shows absorbance of 4% (wt/vol) Accudenz® after overlay with pooled turkey semen (n=10 Beltsville Medium White toms) diluted with 3 mM caffeine in TES-buffered isotonic saline, pH 7.4, containing 25 mM glucose and a 4 mM $CaCl_2(\Delta)$ or the buffer alone ($\circ$) In each case, semen was diluted to $1 \times 10^9$ sperm per milliliter. Three 150-$\mu$L volumes of each sperm suspension were overlaid upon three 1.5 ml volumes of Accudenz®. In each case, the Accudenz® solution had been prewarmed to 41° C. within a polystyrene cuvette. Time zero denotes the time of overlay when the initial reading was made. Thereafter, each cuvette was returned to the water bath. Subsequent readings were made after 5, 10, 20, 30, and 40 min. of incubation at 41° C.

With or without a mobility agonist, turkey sperm penetrated the Accudenz® layer more slowly than did rooster sperm as evidenced by the magnitude and dispersion of absorbance values over time relative to the number of overlaid sperm and a reduction in the Accudenz® concentration from 6 to 4% (wt/vol). The most rapid migration, however, still occurred within the first 5 minutes. Therefore a 5 minute assay could be used to assay turkey sperm. Each symbol represents a mean (n=3). Error bars denote standard deviation. The mobility of turkey sperm in vitro was enhanced by caffeine.

Measurement of poultry sperm mobility by sperm penetration of Accudenz® does not afford information about individual sperm, as do motility studies. Instead the present assay determines mobility, which is more closely related to the sperm population's likelihood of reaching an anatomic location in the female where fertilization will occur.

EXAMPLE 11

Semen donors (n=5 per phenotype) were selected from two groups of individually caged 30-wk-old New Hampshire roosters categorized as having average (n=18) or highly mobile sperm (n=17) by repeated measure analysis, as in Froman and McLean, *Poultry Science* 75:776–784 (1996). Selection criteria were a consistent mobility score as determined by coefficient of variation and a mean mobility score (n=3 observations per male) that fell within the ranges shown in FIG. 1. During the week in which roosters were selected, ejaculates were pooled by phenotype (average or high mobility) and differential sperm mobility confirmed.

Individually caged 30-wk-old New Hampshire hens (n=120) were assigned randomly to be inseminated with pooled, extended semen from either the average or high sperm mobility roosters. Hens were inseminated weekly for 14 consecutive weeks. On each occasion, ejaculates were pooled by phenotype in a graduated 15 ml glass centrifuge tube. Semen was transported to the laboratory at a temperature of 20° to 25° C. Upon arrival in the laboratory, live sperm concentration was determined fluorometrically (Bilgili and Renden, 1984), and neat semen was diluted to $0.5 \times 10^9$ sperm per ml with 111 mM NaCl buffered with 50 mM N-tris-[hydroxymethyl]methyl-2-amino-ethanesulfonic acid (TES), pH 7.4, containing 25 mM glucose and 4 mM $CaCl_2$ (Froman and McLean, 1996). The TES-buffered saline was at room temperature when it was mixed with semen.

Prior to semen collection, 1.5 ml volumes of 6% (wt/vol) Accudenz® were pipetted into each of 2 standard polystyrene cuvettes, each cuvette covered with a 1.5 cm² piece of Parafilm® (VWR Scientific, Seattle, Wash. 98124), and each cuvette placed in a 41° C. water bath. After semen was extended, sperm mobility measurements were made in duplicate according to Froman and McLean (1996). Each cuvette was removed from the water bath and then tapped on the counter top to remove any adherent air bubbles that had formed on the interface between the Accudenz® solution and the inner wall of the cuvette during pre-incubation. Then, the cuvette was blanked at 550 nm by determining absorbance of the Accudenz before the sperm sample was introduced into it. Thereafter, a 150-µL volume of sperm suspension was overlaid on the Accudenz® solution, and the cuvette was returned to the 41° C. water bath. After a 5 minute interval, the cuvette was transferred to the spectrophotometer. The cuvette was allowed to regain equilibrium for one minute after transfer to the spectrophotometer, and absorbance at 550 nm was recorded.

Each sperm suspension was transported to a caged layer facility at 20° to 25° C. in a graduated 15 ml glass centrifuge tube. On the average, approximately 30 minutes elapsed between the start of semen collection and the arrival of extended semen at the caged layer facility. Each hen within a treatment group was inseminated with $50 \times 10^6$ sperm in a volume of 100 µL. All hens within a treatment group were inseminated within 20 minutes, and the centrifuge tube containing the sperm suspension was hand-held during this interval. Following the insemination of hens in one treatment group, semen from the other phenotype was processed and corresponding hens inseminated as above.

Eggs were collected daily, set on a weekly basis, and incubated for 22 days. Hatchability (defined as the number of chicks hatched divided by the total number of eggs set), hatch of fertilized eggs (defined as the number of eggs with an embryo divided by the number of fertilized eggs set), and fertility (defined as the number of eggs with an embryo divided by the total number of eggs set) were determined at the end of the experiment for each hen that remained in lay over the course of the 14-wk egg collection interval. Each proportion was transformed to a modified logit, weighting variables calculated, and each transformed data set analyzed with a log odds model according to Kirby and Froman (1991).

As shown in Table 5, the high sperm mobility phenotype was more fecund ($P \leq 0.001$) than the average sperm mobility phenotype. Hatchability was 10% greater over the course of a 14-wk egg collection interval.

TABLE 5

Differential hatchability and fertility achieved by selecting semen donors based upon in vitro sperm mobility[1]

| Semen Donor Phenotype | Hens[2] (n) | Eggs[3] (n) | Hatchability[4] (%) | Hatch of Fertilized Eggs[5] (%) | Fertility[6] (%) |
|---|---|---|---|---|---|
| Average Sperm Mobility | 55 | 3,818 | 77 ± 1.9[A] | 90 ± 2.2 | 85 ± 1.6[A] |
| High Sperm Mobility | 55 | 4,122 | 87 ± 1.2[B] | 82 ± 1.0 | 95 + 0.7[B] |

[A,B] means a significant difference within a column.
[1] Measured by sperm penetration of 6% (wt/vol) Accudenz ® at 41° C. from an overlay of extended semen.
[2] Each New Hampshire hen was inseminated weekly for 14 consecutive weeks with a dose of $50 \times 10^6$ sperm in a volume of 100 µL.
[3] Collected daily and set weekly.
[4,5,6] Each value is a mean ± SEM.

EXAMPLE 12

Representative males were selected from the average and high sperm mobility phenotypes identified by Froman and McLean, *Poul. Sci.* 75:776–778 (1996), which is incorporated by reference. These are the same methods disclosed in Example 8 above. After confirming differential sperm mobility when ejaculates were pooled by phenotype in preliminary work, a long-term fertility trial was initiated in which the primary end-point was hatchability. In this Example, fertility was determined by the percentage of eggs laid by the inseminated hens that hatched. The effect of sperm mobility on fertility was evaluated in an experiment in which the effect of insemination dose was evaluated as well (Table 4). These data sets illustrate that fecundity of the male is more dependent upon sperm quality than sperm quantity. With this in mind, it is noteworthy that phenotypic distinctions were independent of time.

TABLE 4

Comparative fertility of rooster phenotypes according to insemination dose

| Semen Donor Phenotype | Insemination Dose (×10⁻⁶) (n) | Hens[2] (n) | Eggs[3] (n) | Fertility[4] (%) |
|---|---|---|---|---|
| Average Sperm Mobility | 25 | 42 | 827 | 79 ± 1.9[c] |
|  | 50 | 41 | 811 | 81 ± 2.2[c] |
|  | 100 | 42 | 828 | 86 ± 1.8[b] |
| High Sperm Mobility | 25 | 45 | 898 | 95 ± 0.9[a] |
|  | 50 | 45 | 887 | 95 ± 0.8[a] |
|  | 100 | 45 | 902 | 96 ± 0.8[a] |

[a,b,c] Means values within a column lacking a common superscript differed ($P \leq 0.05$) based upon an a posteriori comparison among means.
[1] Based upon sperm penetration of 6% (wt/vol) Accudenz ® at 41° C. from an overlay of extended semen.
[2] Each Single Comb White Leghorn hen was inseminated weekly for 3 consecutive weeks with 25, 50, or 100 µL of a sperm suspension containing of $1 \times 10^9$ sperm per ml.
[3] Collected daily and set weekly over a 3-wk interval.
[4] Each value is a mean ± S.E.M.

EXAMPLE 13

Individually caged 47-wk-old Single Comb White Leghorn hens (n-260) were assigned randomly to be inseminated with 25, 50, or 100×10⁶ sperm from either the average or high sperm mobility phenotype. Hens were inseminated weekly for 3 consecutive weeks. On each occasion, sperm mobility was measured as in Example 11, with the following exceptions. Once sperm concentration was determined, a 50-$\mu$L sample of neat semen was removed with an M-250 Microman positive displacement pipet (Rainin Instrument Co., Inc., Woburn, Mass. 01888). This semen was extended to $0.5 \times 10^9$ sperm per ml in a borosilicate culture tube with TES-buffered saline containing 25 mM glucose and 4 mM $CaCl_2$. This sperm suspension was used to conduct the mobility assay.

The remaining neat semen was extended to $1.0 \times 10^9$ sperm per ml in a graduated 15-ml glass centrifuge tube, and this sperm suspension was used for insemination. Each hen was inseminated with a volume of 25, 50, or 100 $\mu$L. Egg collection, incubation, and data analysis were performed as in Example 11, with the exception that fertility was determined by examining the contents of eggs for embryonic development after 4 days of incubation. Transformed data were analyzed with a two-way ANOVA. A posteriori comparisons among means were made with the Student-Newman-Keuls test (Sokal and Rohlf, 1969).

As shown in Table 6, the phenotype difference in fertility observed in the initial experiment was also observed ($P \leq 0.0001$) in a replicate experiment in which the effect of insemination dose was evaluated as well. However, neither an insemination dose effect nor an interaction between sperm mobility and insemination dose was detected ($P \leq 0.05$). Based upon a posteriori comparisons means, the maximal insemination dose, i.e., $100 \times 10^6$ sperm per hen, increased fertility ($P \leq 0.05$) by 7% beyond that observed with the minimal dose of $25 \times 10^6$ sperm per hen in the case of the average sperm mobility phenotype (Table 4). Nonetheless, the fertility obtained with the maximal insemination dose form the average phenotype was 9% less than ($P \leq 0.05$) that obtained with the minimal insemination from the high sperm mobility phenotype.

TABLE 6

Summary of two-way ANOVA testing the effects of sperm mobility and insemination dose on fertility[1]

| Source of variation | Degrees of freedom | Sum of squares | Mean square | F-value |
| --- | --- | --- | --- | --- |
| Sperm Mobility | 1 | 66.256 | 66.256 | 114.42**** |
| Insemination Dose | 2 | 3,102 | 1.551 | 2.68 |
| Mobility by Dose | 2 | 0.462 | 0.231 | 0.40 |

[1]Each of 260 Single Comb White Leghorn hens was inseminated with 25, 50, or 100 × 10⁶ sperm from one of two sperm suspensions on a weekly basis for 3 consecutive weeks. Sperm suspensions were prepared by extending pooled semen from roosters categorized as having average of highly mobile sperm (n = 5 roosters per phenotype).
****$P \leq 0.0001$.

The above disclosure indicates that the invention couples the (1) highly variable tendency of sperm from individual males to penetrate a dense medium with (2) their adherence to a surface underlying the dense medium, or (3) automated detection of surface-bound sperm. The inventor has demonstrated that the mobility of sperm populations can be quantified in vitro, is normally distributed, provides a means of detecting differences among normal, fertile males that cannot be detected with conventional methods of semen evaluation, and serves to identify male birds (such as roosters or turkeys) within a flock that have potential to be highly fecund. This newly discovered trait will allow the assay of the present invention to be applied to enhance efficiency of reproduction, and can also be used to evaluate the quality of cryopreserved semen sold as a commodity.

A good evaluation assay will detect slight as well as large differences. Hence variation of a measured characteristic within a population should be as large as possible, and this variability is measured by the coefficient of variation (CV), which is defined as standard deviation/mean×100. An analysis of different sperm characteristics in a base population of 271 roosters has shown that the assay of the present invention has a CV of 65%, compared to a CV of 6% for sperm morphology, 17% for BCF, 7% for VCL, 21% for VAP, 31% for VSL, 27% for motility, 5% for viability, and 44% for an ATP assay. Hence only the ATP assay would even come close to differentiating among 27 normal, fertile roosters. Conventional motility measurements, with a CV of 27%, were much less able to distinguish members of this population.

As used in the following claims, a physicochemical property of a liquid refers to a physically measurable difference (such as density or viscosity). The barrier medium of the invention has physicochemical properties that impede net movement of the sperm into the barrier medium, unless the sperm have the ability to overcome the physicochemical barrier. The term "net movement" into the barrier medium refers to movement of more sperm into the medium than out of the medium (because sperm move in three dimensions and some will migrate out of the barrier medium). The term "migration" refers to net movement into a medium.

An isotonic medium is one that has substantially similar osmolality to the material in the medium (such as semen). A diluent is a diluting agent. A buffered diluent is one that contains a buffering agent that helps maintain the pH of a solution at a desired pH, such as a physiologic pH.

Having illustrated and described the principles of the invention in several preferred embodiments, it should be apparent to those skilled in the art that the invention can be modified in arrangement and detail without departing from such principles. I claim all modifications coming within the spirit and scope of the following claims.

I claim:

1. A method of measuring mobility of sperm, comprising:
   providing a liquid sperm test specimen;
   providing a liquid barrier medium, in contact with the test specimen, wherein the liquid barrier medium has a greater density than the test specimen;
   maintaining the barrier medium in contact with the test specimen for a sufficient period of time to allow highly mobile sperm to migrate into the barrier medium and separate highly mobile sperm from less mobile sperm; and
   quantitating migration of highly mobile sperm into or through the dense medium.

2. The method of claim 1 wherein providing a barrier medium in contact with the test specimen comprises layering the test specimen on top of the barrier medium, so that sperm from the test specimen migrate downwardly into the barrier medium.

3. The method of claim 2 wherein the density of the barrier medium is at least 1.005.

4. The method of claim 1, wherein the difference in density between the barrier medium and the test specimen is at least 0.005.

5. The method of claim 1, wherein the test animal is an avian male, providing a liquid test specimen comprises diluting a sample of avian sperm in an isotonic, buffered, liquid diluent, and maintaining the barrier medium comprises maintaining the barrier medium at a temperature of 40°–41° C.

6. A method of identifying highly mobile sperm, comprising:

providing a volume of a liquid barrier medium in a container;

layering a volume of a liquid test specimen medium on top of the barrier medium, wherein the liquid test specimen medium comprises a specimen of sperm from a male test subject and a diluent that is isotonic with the specimen of sperm and buffered to a physiologic pH, wherein a density of the barrier medium is sufficiently greater than a density of the test specimen medium to allow highly mobile sperm to migrate into the barrier medium more quickly than sperm that are not highly mobile; and maintaining the barrier medium at a preselected temperature, at which sperm activity is optimal, for a sufficient period of time to allow highly fecund males to be identified by an increased migration of sperm into the barrier medium, as compared to migration of sperm from males that are not highly fecund.

7. The method of claim 6 further comprising automatically quantitating migration of sperm into the separation medium.

8. The method of claim 7 wherein automatically quantitating migration of sperm comprises measuring a change in optical density of the separation medium, and correlating the change in optical density to a quantity of sperm that have migrated into or through the separation medium.

9. The method of claim 7 wherein automatically quantitating migration of sperm into the separation medium comprises providing a collection member below the separation medium, wherein the collection member adheres the sperm.

10. The method of claim 9, wherein the collection member is coated with a binding material selected from the group consisting of extracts from a vitelline membrane of turkey or chicken eggs to which poultry sperm adhere, and a polycationic material.

11. A method of identifying highly fecund avian males, comprising the steps of:

providing a volume of a liquid barrier medium in a container:

layering a volume of a liquid test specimen medium on top of the barrier medium, wherein the liquid test specimen medium comprises a specimen of sperm from a male avian test subject and a diluent that is isotonic with the specimen of sperm and buffered to a physiologic pH, wherein a density of the barrier medium is greater than a density of the test specimen medium;

maintaining the barrier medium at a preselected temperature, at which sperm activity is optimal, for a sufficient period of time to allow highly fecund males to be identified by an increased migration of sperm into or through the barrier medium, as compared to migration of sperm from males that are not highly fecund;

automatically quantitating migration of sperm into the barrier medium, which comprises providing a collection member below the barrier medium, wherein the collection member is coated with a binding material selected from the group consisting of extracts from a vitelline membrane of turkey or chicken eggs to which poultry sperm adhere, and a polycationic material;

wherein the barrier medium comprises a 2–10% aqueous solution of 5-(N-2,3-dihydroxypropylacetamidol)-2,4, 6-triido-N,N'-bis(2,3 dihydroxypropyl)isophthalamide.

12. A method of identifying highly fecund poultry, comprising the steps of:

placing a collection member in a collection vessel, wherein the collection member comprises a protein extract from the vitelline membrane of turkey or chicken eggs to which poultry sperm adheres;

providing a layer of liquid barrier medium on the collection member in contact with the protein extract, and the barrier medium comprises a biologically inert material;

layering a volume of a test specimen medium on top of the barrier medium, wherein the test specimen medium comprises a specimen of sperm from a male avian test subject and a diluent that is isotonic with the specimen of sperm and buffered to a physiologic pH, wherein a density of the barrier medium is sufficiently greater than a density of the test specimen medium to allow net movement of highly mobile sperm into the barrier medium more than net movement of sperm that are not highly mobile;

maintaining the barrier medium at a preselected temperature of 40°–41° C. for a sufficient period of time to allow highly fecund males to be identified by an increased migration of sperm into the barrier medium, as compared to migration of sperm from males that are not highly fecund.

removing the test specimen and barrier medium from the collection member;

washing the collection member;

quantitating a quantity of sperm adhered to the collection member; and correlating the quantity of sperm with fecundity of the test subject.

13. The method of claim 10, wherein the barrier medium comprises a 2–10% aqueous solution of 5-(N-2,3-dihydroxypropylacetamidol)-2,4,6-triido-N,N'-bis(2,3 dihydroxypropyl)isophthalamide.

14. The method of claim 12, wherein the diluent has an osmolality of 290–325 mmol/kg of solution, and is buffered to a pH of about 7.4, and the density of the barrier medium is at least 0.005 greater than the density of the test specimen.

15. A device for measuring mobility of sperm, comprising:

a container;

a temperature regulator for maintaining the container at a preselected temperature;

a volume of a liquid separation medium in the container;

a volume of a liquid test specimen medium on top of the separation medium in the container, wherein the test specimen medium comprises a specimen of sperm from a male test subject and a diluent that is isotonic with the specimen of sperm and buffered to a physiologic pH, wherein a density of the separation medium is sufficiently greater than a density of the test specimen medium to allow highly mobile sperm to migrate into the separation medium more quickly than sperm that are not highly mobile; and a suction device positioned to suction the test specimen and separation medium from the container after a preselected period of time.

16. The device of claim 15, further comprising an automated device for quantitating a number of sperm that migrate into or through the barrier medium.

17. The device of claim 16, wherein the automated device comprises a spectrophotometer that measures an optical density of the barrier medium.

18. The device of claim 16, wherein the automated device comprises a collection member coated with a protein that adheres avian sperm, and the barrier medium is layered on top of the collection medium.

19. The device of claim 18, wherein the suction device comprises a piston that is advanced into the container, and a cannula on the piston that suctions the test specimen and barrier medium out of the container as the piston is advanced into the container.

20. The device of claim 19, further comprising a guide member that extends from the piston into the container as the piston is advanced into the container, and an opening in the guide member in communication with a source of flushing liquid to wash off the collection member.

21. A test kit for selecting highly mobile sperm, comprising:
- a container;
- a temperature regulator for maintaining the container at a preselected temperature;
- a volume of a liquid separation medium for placement in the container;
- a volume of a liquid test specimen medium for placement on top of the separation medium in the container, wherein the test specimen medium comprises a medium for suspending a specimen of sperm from a male avian test subject, and a diluent that is isotonic with the specimen of sperm and buffered to a physiologic pH, wherein a density of the separation medium is sufficiently greater than a density of the test specimen medium to allow highly mobile sperm to migrate into the separation medium more quickly than sperm that are not highly mobile;
- a suction device positioned to suction the test specimen and separation medium from the container after a preselected period of time; and
- an automated device for quantitating a number of sperm that migrate into or through the separation medium.

22. A device for identifying highly mobile avian sperm, comprising:
- a container;
- a temperature regulation well in which the container fits to maintain the container and its contents at about 40°–41° C.;
- a collection member comprising a substrate including a protein extract from the vitelline membrane of turkey or chicken eggs that adheres avian sperm, wherein the collection member is positioned at a bottom of the container and retained in position with a retention ring;
- a layer of liquid separation medium on the collection member, and the separation medium comprises a biologically inert material;
- a layer of liquid test specimen medium on top of the separation medium, wherein the test specimen medium comprises a specimen of sperm from a male avian test subject and a diluent that is isotonic with the specimen of sperm and buffered to a physiologic pH, wherein a density of the separation medium is sufficiently greater than a density of the test specimen medium to allow highly mobile sperm to migrate into or through the separation medium more quickly than sperm that are not highly mobile; and
- a suction device for suctioning the test specimen medium and the separation medium from the container, the suction device comprising a telescopic guide member positioned to abut against the retention ring as the suction device is advanced into the container, and a suction cannula that extends below the guide member, wherein the telescopic guide member telescopes into itself to a shortened condition when an abutment pressure against the retention ring exceeds a preselected value, and an liquid outlet from the guide member is opened when the guide member is in the shortened condition to introduce a flushing liquid from the guide member on to the collection member.

23. A method of identifying highly mobile sperm, comprising:
- providing a volume of liquid barrier medium in a container, the liquid barrier medium comprising 5-(N-2,3-dihydroxypropylacetamidol)-2,4,6-triido-N,N'-bis (2,3 dihydroxypropyl)isophthalamide;
- layering a volume of liquid test specimen medium on top of the liquid barrier medium, wherein the liquid test specimen medium has a density less than a density of the liquid barrier medium; and
- quantitating migration of sperm into the barrier medium.

24. The method of claim 23, wherein quantitating migration of sperm into the liquid barrier medium comprises measuring a physical property of the barrier medium that corresponds to the number of sperm in the barrier medium.

25. The method of claim 24, wherein quantitating migration of sperm into the liquid barrier medium comprises measuring an optical property of the barrier medium.

26. A device for measuring mobility of sperm, comprising:
- a container;
- a volume of a liquid separation medium in the container; and
- a volume of a liquid test specimen medium in contact with the liquid separation medium, wherein the test specimen medium comprises a specimen of sperm and a diluent, and the separation medium is of a density sufficiently greater than a density of the test specimen medium to allow highly mobile sperm to migrate into the separation medium more quickly than sperm that are not highly mobile.

27. The device of claim 26, further comprising a suction device positioned to suction the test specimen and separation medium from the container after a preselected period of time.

28. A test kit for selecting highly mobile sperm, comprising:
- a container;
- a volume of a liquid separation medium for placement in the container;
- a volume of a liquid test specimen medium for placement in contact with the separation medium in the container, wherein the test specimen medium comprises a medium for suspending a specimen of sperm from a male test subject, and the separation medium has a density that is sufficiently greater than a density of the test specimen medium to allow highly mobile sperm to migrate into the separation medium more quickly than sperm that are not highly mobile; and
- an automated device for quantitating an amount of sperm that migrate into or through the separation medium.

29. The device of claim 28, wherein the liquid test specimen medium is immediately on top of and in continuous contact with the liquid separation medium, along a separation interface between the test specimen medium and separation medium.

30. The device of claim 29, further comprising a collection member positioned at a bottom of the container immediately below the liquid separation medium, and a suction device for suctioning the test specimen medium and the separation medium from the container, the suction device comprising a cannula that extends below the test specimen medium to abut the collection member, but which telescopes into itself to a shortened condition when an abutment pressure against the suction device exceeds a preselected value, so that a liquid outlet from the guide member is opened when the guide member is in the shortened condition to introduce a flushing liquid from the guide member on to the collection member.

31. The device of claim 28, wherein the liquid separation medium comprises 5-(N-2,3-dihydroxypropylacetamidol)-2,4,6-triido-N,N'-bis(2,3 dihydroxypropyl)isophthalamide.

* * * * *